United States Patent [19]

Urheim

[11] Patent Number: 4,867,177

[45] Date of Patent: Sep. 19, 1989

[54] VAGINAL DRAPE, INSERTION UNIT AND KIT

[75] Inventor: John E. Urheim, Lincolnshire, Ill.

[73] Assignee: Gynex, Inc., Deerfield, Ill.

[21] Appl. No.: 50,888

[22] Filed: May 15, 1987

[51] Int. Cl.⁴ .............................................. A61F 13/00
[52] U.S. Cl. .................................... 128/849; 128/856
[58] Field of Search ................... 128/50, 130, 132 D, 128/156, 132 R, 849–856

[56] References Cited

U.S. PATENT DOCUMENTS

| | | | |
|---|---|---|---|
| 1,503,117 | 7/1924 | Crawford et al. | 2/50 |
| 3,703,896 | 11/1972 | Nuwayser | 128/130 |
| 4,188,945 | 2/1980 | Wenander | 128/132 D |
| 4,570,627 | 2/1986 | MacConkey et al. | 128/132 D |
| 4,598,004 | 7/1986 | Heinecke | 128/156 |

*Primary Examiner*—Robert A. Hafer
*Assistant Examiner*—Michael Brown
*Attorney, Agent, or Firm*—Baker & McKenzie

[57] ABSTRACT

A vaginal drape having a substantially frustoconical configuration, and a perimeter expandable along the length thereof. The drape is adapted to be secured about the cervix uteri of a human female. The vaginal drape can be used alone or in cooperation with an insertion unit or a kit for conducting medical and/or surgical procedures on the uterus. The drape provides an aseptic region while a medical procedure is being performed on the uterus through the vaginal canal.

3 Claims, 2 Drawing Sheets

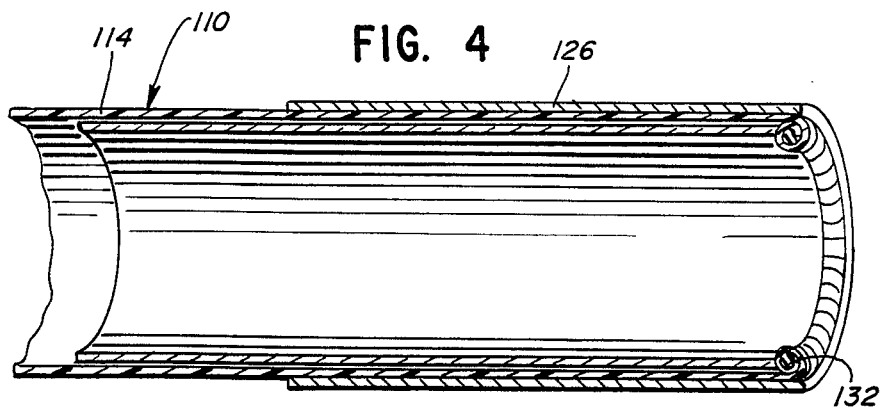
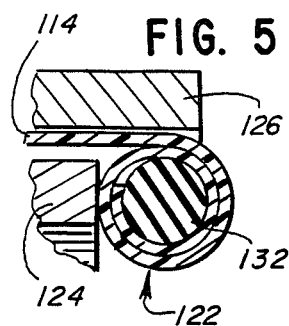
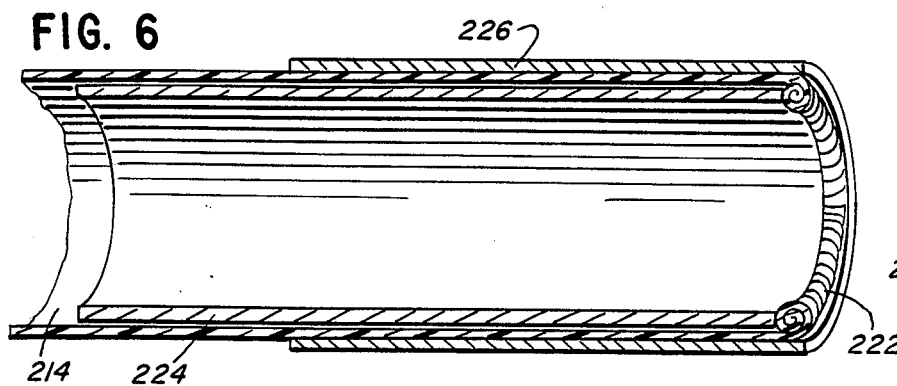
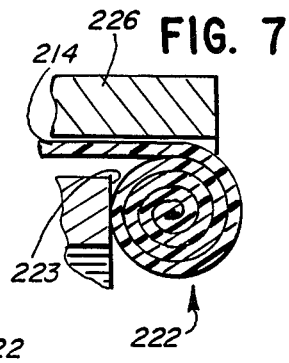
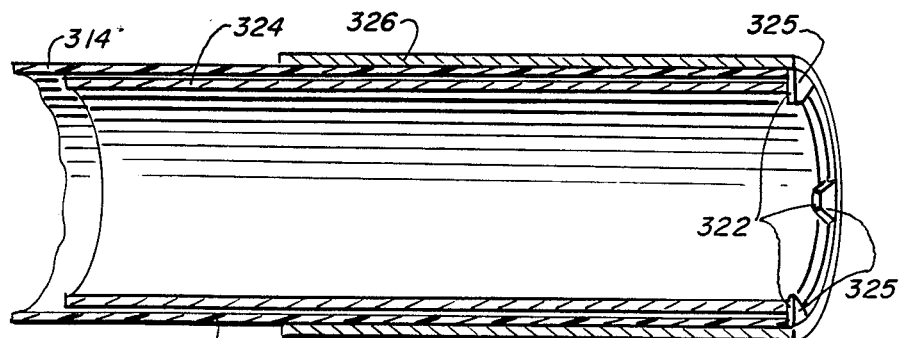
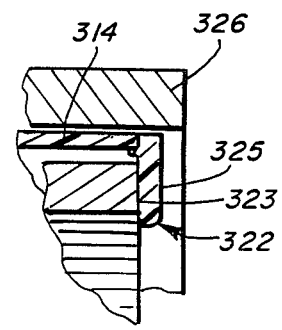
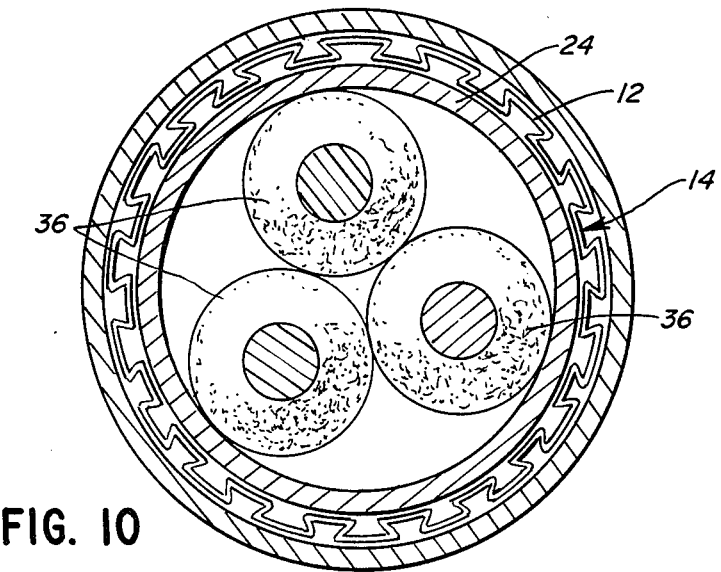

VAGINAL DRAPE, INSERTION UNIT AND KIT

TECHNICAL FIELD

The present invention relates to medical equipment, and more particularly to a tubular surgical drape for creating a sterile environment when conducting a medical procedure on a patient.

BACKGROUND OF THE INVENTION

It has long been known that the uterus of a human female is a sterile environment while the vaginal canal is not. There are many surgical procedures that require passage through the vaginal canal to gain access to the uterus through its cervix (the cervix uteri). For example, the normal insertion of an intrauterine contraceptive device (IUD) is invasive of the uterus via the vaginal canal.

Current practice generally suggests that the physician swab the cervical os with a sterilizing agent, such as betadine, prior to performing an invasive surgical procedure. However, because the surrounding vaginal canal is not sterile, it is extremely difficult to preserve an aseptic technique.

A recent study (see Jacques et al., Am. J. Obstet. Gynecol. 154:648-655, March 1986) has shown that insertion of an IUD through the vaginal canal appears to be a significant cause in the introduction of microorganisms into the uterus. Once microorganisms have entered the uterus, the incidence of pelvic inflammatory disease increases. The study suggested that the IUD's passage through the vaginal canal immediately prior to placement in the uterus is a primary reason of microbial colonization of IUDs.

The present invention facilitates the performance of an invasive surgical procedure to be performed on the human female uterus with a reduced likelihood for microorganism invasion.

SUMMARY OF THE INVENTION

The present invention contemplates a tubular vaginal drape, a drape insertion unit, and a kit for use in conducting medical and/or surgical procedures on the uterus. The vaginal drape helps to maintain an aseptic environment during such procedures.

More specifically, the vaginal drape of the present invention is a gathered or pleated sheet-form tube, i.e., a tube having a foreshortened but expandable periphery. Typically, the tube is made of conventional surgical drape material or the like, and is provided at one end with a special securement means. The tube is open at both ends. At one end, the opening is free-form and can expand to the full circumference of the tube. At the other end, a relatively smaller opening is defined by a peripheral lip such as a flange or a seam. The lip provides a securement means for the drape about the cervix uteri and projects inwardly from the tube.

The relatively smaller opening or aperture is situated at the distal end of the tubular drape relative to the physician. The distal end of the tubular drape is the end to be placed within the vaginal canal of a human female patient and positioned about the cervix. When in place, the tube is expanded as permitted by the geometry of the vaginal canal to provide an aseptic access route to the cervix. The gathered or pleated wall of the vaginal drape protrudes beyond the body cavity. The protruding material portion may be slit to facilitate the positioning of the drape, and/or portions thereof may be rolled up or folded back to conform to the patient.

The distal end of the vaginal drape is retained within the vaginal canal by a securement means such as a bioadhesive, a mechanical attachment means, e.g., a ring stretchable around the cervix or a ring that expands and lodges in the fornices of the vaginal canal, or the like expedients. The securement means temporarily retains the vaginal drape about the cervix while a desired surgical procedure is performed. The drape is removed easily after the procedure.

The vaginal drape can be packaged alone or together with an insertion unit. In the latter case, the insertion unit is constituted by an inner, dispensing cylinder, an outer, retaining cylinder, and the vaginal drape in gathered or pleated form is situated therebetween. The vaginal drape preferably remains gathered or pleated and in a compact, compressed form for shipping and storage by the coaction of the retaining cylinder with the dispensing cylinder.

The insertion unit provides a convenient means for a physician to install the vaginal drape. In particular, the dispensing cylinder is first manipulated to remove the drape from the retaining cylinder and then to position the aperture of the vaginal drape around the cervix uteri.

The dispensing cylinder is pushed through the outer, retaining cylinder while urging the drape into the vaginal canal and allowing the drape material to expand. Once the vaginal drape is secured in place, the inner, dispensing cylinder is removed and the region is ready for a surgical procedure. During insertion, the bore of the dispensing cylinder provides a sighting means for positioning of the drape about the cervix.

With the vaginal drape in place and the cylinders removed, the exposed portion of the cervix is disinfected, thereby creating a sterile environment that reduces the likelihood of an inadvertent introduction of microorganisms into the uterus.

The drape can be sterilized immediately prior to use. Alternatively, to maintain the sterile qualities of a pre-sterilized vaginal drape, a sealed vaginal drape kit can be provided. Such a kit includes the vaginal drape together with the dispensing cylinder and the retaining cylinder contained within a hermetically sealed envelope or pouch. Optionally, the kit may include medical swabs impregnated with a sterilizing agent such as betadine.

Special kits can be provided for specific surgical procedures such as for the insertion of an intrauterine device (IUD). In such instances the IUD can be packed in the kit, if desired. The drape may also be used and kits assembled for other surgical procedures on other parts of the body.

Numerous other advantages and features of the invention will become readily apparent from the following detailed description of the invention, the accompanying drawings, and the claims.

BRIEF DESCRIPTION OF THE DRAWINGS

FIG. 4 is a cross-sectional view showing an insertion unit, the vaginal drape being interposed between the cylinders and provided with a ring-type securement means;

FIG. 5 is an enlarged cross-sectional view showing the coaction of the elements of this invention in the embodiment illustrated in FIG. 4;

FIG. 6 is a cross-sectional view of the insertion unit illustrating an alternative preferred embodiment of the present invention;

FIG. 7 is an enlarged cross-sectional view showing the coaction of the elements of the invention illustrated in the embodiment of FIG. 6;

FIG. 8 is a cross-sectional view of the insertion unit illustrating yet another preferred embodiment of the present invention;

FIG. 9 is an enlarged cross-sectional view showing the coaction of the elements of the invention illustrated in the embodiment of FIG. 8; and FIG. 10 is a cross-sectional view taken along plane 10—10 of FIG. 2 and showing the kit suitable for conducting a medical procedure through the vaginal canal of a human female.

DESCRIPTION OF THE PREFERRED EMBODIMENTS

Figure 1:
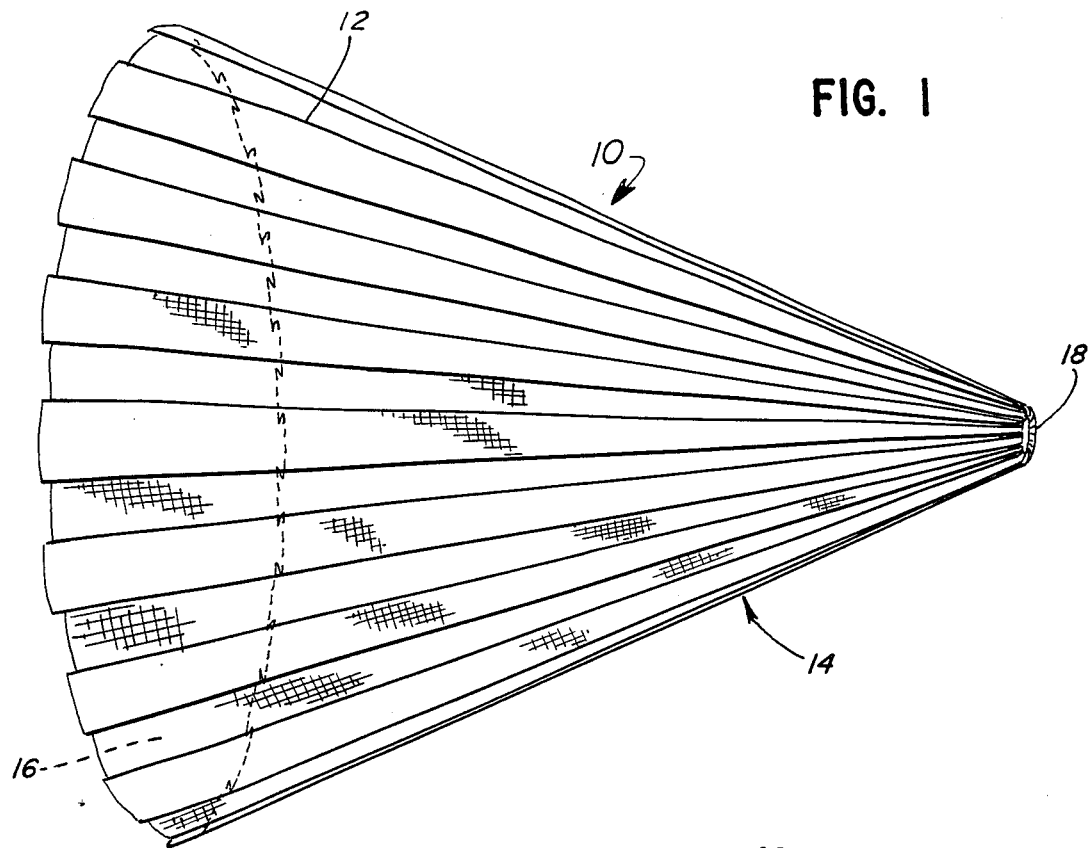
FIG. 1 is a perspective view of a vaginal drape embodying this invention.

While this invention is susceptible of embodiment in many different forms, there is shown in the drawing and will be described hereinbelow in detail certain embodiments thereof with the understanding that the present disclosure is to be considered as an exemplification of the principles of the invention and does not limit the invention to the illustrated embodiments.

Referring to the drawing, FIG. 1 shows an embodiment of the vaginal drape 10 of the present invention. The drape is a sheet-form tube 14 provided with a plurality of gathers, pleats or the like 12 which extend substantially the full length of the drape. These gathers or pleats foreshorten the periphery of the sheet-form tube as packaged or stored, but permit an expansion of the perimeter of the tube along its length as required during use. Creping also can be utilized for this purpose. The tube 14 can be made from various types of sheet-form materials such as nonwoven fabrics, common to the medical industry or may be made of an alternate material, for example, a clear polyethylene or polyethylene terephthalate film, and the like.

Figure 2:
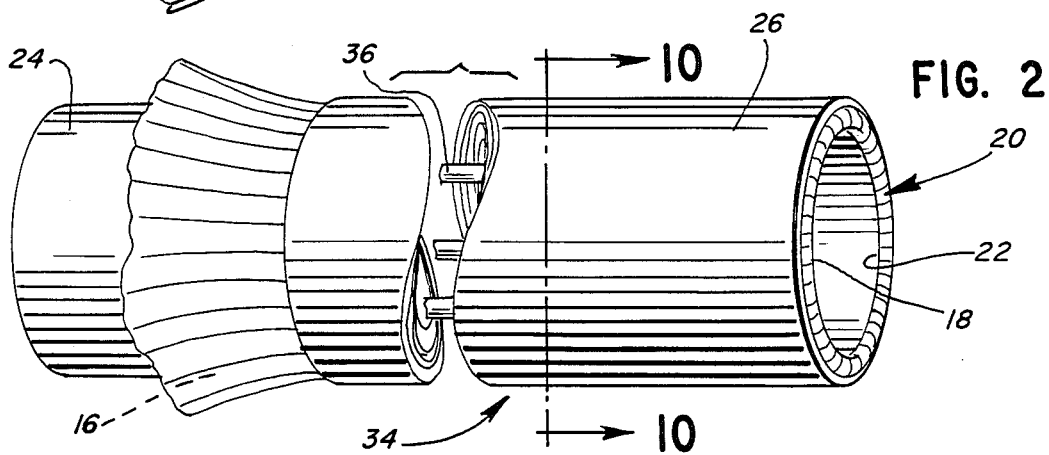
FIG. 2 is a fragmentary perspective view of the insertion unit in its shipment and storage configuration.

The tube 14 is open at both ends. At one end, the distal end of the drape, the gathers or pleats 12 are captured and contained around a relatively smaller opening or aperture 18. At the opposite or proximal end, the gathers or pleats are free and define a relatively larger, free-form opening 16. As shown in FIG. 2, at distal end 18 there is provided a lip 22 which is located about the periphery of the tube 14. Lip 22 projects inwardly from tube 14. Also located at the distal end defining aperture 18 is a securement means 20 which performs the dual purpose of retaining the foreshortening gathers or pleats 12 in compacted form while securing the vaginal drape 10 to the human female's cervix.

Lip 22 can be solely a structural element of the drape, with another element acting as the securement means 20. Alternatively, the lip 22 and the securement means 20 can be combined in a single structural element. In some embodiments of this invention only a securement means 20 is necessary. The several embodiments shown in FIGS. 4–9 and discussed hereinbelow illustrate various securement means and retaining lips such as flanges and the like.

Figure 3:
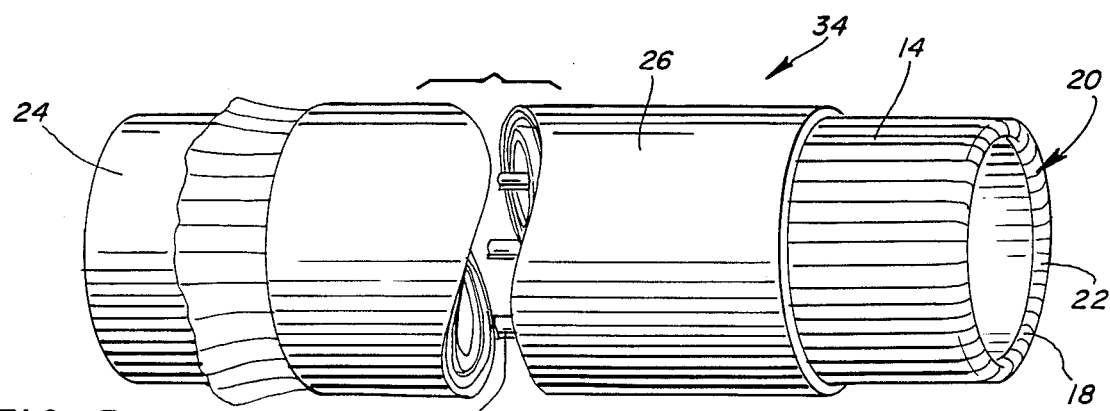
FIG. 3 is a fragmentary perspective view of the insertion unit with a portion of the vaginal drape exposed as during a typical insertion.

FIG. 2 shows the drape insertion unit 34 in a shipping or storage configuration, while FIG. 3 shows unit 34 with drape 10 partially withdrawn. The insertion unit 34 includes an outer, retaining cylinder 26 and an inner, dispensing cylinder 24. The vaginal drape 10 is interposed in a compact manner between the inner dispensing cylinder 24 and the outer, retainer cylinder 26. Also shown in FIG. 2 are swabs 36 which are an optional accessory of the vaginal drape kit hereinbelow discussed in connection with FIG. 10.

Preferably, retaining cylinder 26 is shorter than the dispensing cylinder 24. The preferred embodiment includes a retaining cylinder 26 that completely surrounds at least the distal portion of the tube 14, causing the gathers or pleats 12 to remain compact and a dispensing cylinder that is at least about twice as long as the retaining cylinder.

The lip 22 coacts with one end, the distal end, of the dispensing cylinder 24 to dispense and position the drape 10 from within the retaining cylinder 26. Once the drape 10 is in position, the dispensing cylinder 24 can urge the securement means 20 about or over the cervix uteri, depending upon the nature of the desired securement. Swabs 36 can be stored within the chamber defined by dispensing cylinder 24 as shown in FIGS. 2 and 10.

The size of aperture 18 can vary depending upon the size of cervix to be accommodated. Typically, the diameter of aperture 18 is about 3 to about 5 centimeters.

FIGS. 4 through 9 illustrate flanges, securement means, and their coaction with the retaining and dispensing cylinders.

FIGS. 4 and 5 show a flexible ring 132 as the securement means. The flexible rig 132 provides both the abutment lip and the securement means. The flexible ring 132 is attached about the aperture of the pleated tube 114 in a seam of the tube material.

In this manner, securement means are provided without additional structural elements. First, the flexible ring 132 can be elastic and stretchable, so that the exposed portion of the cervix may be drawn into the ring 132 while the latter is stretched or expanded. The ring 132 causes the mucus membrane of the cervix uteri to be temporarily slightly compressed; however, the temporary compression is not so great as to impede the access to the uterus via the cervix but is sufficient to maintain the vaginal drape 110 in place during a medical procedure.

Secondly, depending upon size, flexible ring 132 can be slightly compressed while contained within the retaining cylinder. Once the outer, retaining cylinder 126 is removed, ring expands and lodges in the fornices surrounding the cervix.

Also illustrated by FIG. 5, the flexible ring 132 defines, together with the drape material, a flange 122 upon which a bioadhesive is applied. The bioadhesive serves as the securement means. The drape is positioned by applying pressure against the ring 132 to engage the bioadhesive with tissue contiguous thereto. Suitable bioadhesives are discussed in detail hereinbelow.

In the embodiment illustrated by FIGS. 6 and 7, pleated tube 214 is rolled at its cervix-enveloping end to form a built-up seam 222 which abuts the distal end 223 of dispensing cylinder 224. The built-up seam 222 can have sufficient elasticity to attach to the cervix, or seam 222 can be coated or impregnated with a suitable bioadhesive. During storage, seam 222 is contained within retaining cylinder 226.

Yet another embodiment of the present invention is shown in FIGS. 8 and 9. Pleated drape 314 is contained between retaining cylinder 326 and dispensing cylinder 324. The cervix-encompassing end of drape 314 is provided with peripherally spaced, inwardly extending protuberances 322 that provides an abutment means for distal end 323 of dispensing cylinder 324 as well as an opposite exposed surface or land such as 325 that is coated with a bioadhesive to provide a securement means to body tissue within the vaginal canal.

The drape insertion unit retains the vaginal drape in a foreshortened and a compressed form for shipping and storage. When the drape is to be inserted, the vaginal canal is first opened with a surgical instrument, typically a speculum. Then the insertion unit is placed at or inside the canal as needed, with the dispensing cylinder guiding the vaginal drape to and about the cervix. The retaining cylinder is pulled off the dispensing cylinder in a direction opposite the cervix. FIG. 3 illustrates the manner in which the retaining and dispensing cylinders can be axially shifted, one relative to the other, to effect placement of the vaginal drape. The dispensing cylinder 24 guides the drape and its corresponding securement means to the cervix. Once the drape is secured to or about the cervix, the inner cylinder 24 is removed, the cervix swabbed with a sterilizing agent, and the region is ready for a surgical procedure.

FIG. 3 also shows the swabs 36 which are a part of the vaginal drape kit herein below discussed in connection with FIG. 10.

In the embodiments that use a bioadhesive to secure the vaginal drape 10 to the mucus membrane of the cervix itself, a number of bioadhesives are available for use. Such bioadhesives are chemical compounds that adhere to human mucus membrane and have long been used to attach dentures to the mucus membrane of the gums. Illustrative bioadhesives are available in many forms, for example, sodium carboxymethylcellulose (NaCMC) dispersed in various polymers, then formed into thin films. Another, paste-like bioadhesive is NaCMC in a polyethylene/mineral oil gel base. Suitable other bioadhesives are described in Gurny et al., Biomaterials 5:336-340, (November, 1984); Ch'ng et al., J. Pharm. Sci 74 (4):399-405, (April 1985); and Hui et al., Int. J. Pharmaceutics 26:203-213 (1985).

The vaginal drape can be sterilized immediately prior to use. Alternatively, to preserve the sterile qualities of a pre-sterilized vaginal drape, a sealed kit can be provided. The kit is hermetically sealed by a wrapping so that sterile conditions are preserved through shipping and storing. The wrapping can be a film or other sheet-form envelope, preferably one permeable to a sterilizing gas. Preferably, the wrapping is heat-sealable or heat-shrinkable for ease of packaging. Such a kit includes the insertion unit 34, with the inner, dispensing cylinder 24, the outer, retaining cylinder 26, the vaginal drape 10. A cross section of such a kit is shown in FIG. 10. Included in the illustrated kit are plural cleansing swabs 36 nested inside the inner dispensing cylinder 24. Swabs 36 can be impregnated with a sterilizing agent, such as betadine, if desired.

These kits can be assembled to include other single use devices or instruments used when conducting a medical procedure through the vaginal canal. For example, in an IUD insertion, an IUD could be packaged as part of the kit.

From the foregoing, it will be observed that numerous variations and modifications may be effected without departing from the true spirit and scope of the novel concept of the invention. It is to be understood that no limitation with respect to the device illustrated herein is intended or should be inferred. It is, of course, intended to cover by the appended claims all such modifications as fall within the scope of the claims.

I claim:

1. A sterile vaginal drape structure comprising:
   (A) a flexible tube having a proximal end and a distal end, and a circumferential wall having defined therein a plurality of pleats which:
      extend substantially the full length of said tube;
      are in an initially folded configuration;
      are captured and contained about said distal end but are free at said proximal end; and
      are unfolded to produce a configuration the distal end of which is adapted to be received within the vaginal canal of a human female while the proximal end defines a relatively larger, free-form opening; and
   (B) securement means functionally associated with said distal end which retains at said distal end said pleats in said folded configuration and which detachably associates said distal end about the cervix uteri of said human female, said securement means including an inwardly extending flange adapted to surround said cervix uteri; and
   (C) said proximal end being expandable to the full unfolded circumference of said tube.

2. The vaginal drape structure of claim 1, wherein said securement means comprises a flexible ring of a size adapted to receive said cervix uteri.

3. The vaginal drape structures of claim 1 wherein said flange is provided with a bioadhesive.

* * * * *